United States Patent [19]

Nakagawa

[11] Patent Number: 4,650,323

[45] Date of Patent: Mar. 17, 1987

[54] SUGAR CONCENTRATION GAUGE

[76] Inventor: Susumu Nakagawa, 3-28 Izumino-cho 2-chome, Kanazawa-shi, Ishikawa-ken, Japan

[21] Appl. No.: 814,721

[22] Filed: Dec. 30, 1985

[30] Foreign Application Priority Data

Dec. 30, 1984 [JP] Japan ................................ 59-280643

[51] Int. Cl.$^4$ ............................................. G01N 21/41
[52] U.S. Cl. .................................................... 356/135
[58] Field of Search ................ 356/128, 135, 136, 137

[56] References Cited

U.S. PATENT DOCUMENTS 2,601,128 6/1952 Rosenthal et al. ................... 356/137

FOREIGN PATENT DOCUMENTS 53-1582 1/1978 Japan .
58-12847 1/1983 Japan .
81/00152 1/1981 PCT Int'l Appl. ................. 356/128

Primary Examiner—F. L. Evans
Attorney, Agent, or Firm—Wenderoth, Lind & Ponack

[57] ABSTRACT

A sugar concentration gauge of a type for measuring the sugar concentration of test liquid applied to a light incidence surface of a prism through detection of a refraction angle, with which a light beam having passed through the test liquid is emitted from the prism and which corresponds to the sugar concentration of the test liquid. The gage has a movable plate capable of adjustment with respect to the light incidence surface of the prism, a light incidence plate on the movable plate so as to be superposed on the light incidence surface of the prism, and a weight on the movable plate for exerting a vertical load onto the light incidence surface of the prism, whereby the test liquid can be uniformly spread on the light incidence surface of the prism without being influenced by the kind and amount of the test liquid.

3 Claims, 11 Drawing Figures

SUGAR CONCENTRATION GAUGE

FIELD OF THE INVENTION AND RELATED ART STATEMENT

The present invention relates to a sugar concentration gauge for measuring the sugar content in fruits or like.

There have heretofore been proposed various sugar concentration gauges for measuring sugar concentration, such as in Japanese Patent Public Disclosure No. 53-1582 and Japanese Utility Model Public Disclosure No. 58-12847, etc. FIG. 1A illustrates a prior art gauge of an eyepiece type utilizing a prism 1. The prism 1 has first, second and third surfaces 2, 3 and 4 serving respectively as a light incidence surface, a colored reflecting surface and a light emission surface. Liquid 5 to be tested is applied to the entire light incidence surface 2. A light beam passed through the test liquid 5 is transmitted through the prism 1 is emitted from the light emission surface 4 with an angle of refraction corresponding to the sugar concentration of the test liquid. A light beam $P_1$ which is emitted after being reflected by the colored reflecting surface 3 and a light beam $P_2$ which is emitted without being reflected by the colored reflecting surface 3 are transmitted to a gauge plate 6. A position, at which a border line P between colored light and white light crosses a scale 7 on the gauge plate 6, is read as the sugar concentration (FIG. 1B).

With this sugar concentration gauge, however, it is very different to observe the border line since the border line between the bright and dark sections is observed with a single eye through a small eyepiece window. The field of sight directed to the border line varies with the orientation or angle of the eye facing the eyepiece. Furthermore, since the border line is actually a semi-dark section belonging neither to the bright section nor to the dark section, it is difficult to ascertain an accurate border line which may bring about an error. The gauge is also inconvenient to handle. Furthermore, the film of the test liquid 5 applied to the light incidence surface 2 of the prism 1 is liable to have thickness fluctuations, resulting in non-uniform transmission of light. When the test liquid 5 is excessively thick, the transmitted light is extremely reduced, thereby leading to errors of measurement. For these reasons, highly reliable measurement of the sugar concentration cannot be expected. The drawbacks described above are particularly pronounced when the test liquid 5 has high viscosity.

Furthermore, since the sugar concentration gauge illustrated in FIGS. 1A and 1B utilizes natural light as the source of light beams transmitted through the test liquid 5, the measurement is impossible in a dark ambient condition. Also since natural light which contains components of various intensities and wavelengths is utilized as the source of light, the measurement is subjected to errors depending on such conditions as the place and time of measurement.

Still further, since the light incidence surface 2 of the prism 1 is exposed to the outside so that light is incident on the prism 1 in all directions, external disturbances are liable to be introduced.

OBJECT AND SUMMARY OF THE INVENTION

The present invention has been accomplished in order to preclude the drawbacks as described above.

One object of the present invention is to provide a sugar concentration gauge capable of preventing thickness fluctuations or excessive thickness of a test liquid film applied to the prism surface for preventing non-uniform or reduced transmission of light to an optical system even when the test liquid has high viscosity and for permitting thin test liquid to be applied uniformly to the light incidence surface of the prism to effectively eliminate errors of the measurement.

Another object of the present invention is to provide a sugar concentration gauge in which a light-blocking cover can be closed so that a light incidence plate and a light source lamp are immediately set in position relative to the prism to facilitate sugar concentration measurement.

Still another object of the present invention is to provide a sugar concentration gauge which permits highly stable and reliable measurement of the sugar concentration regardless of whether the ambient condition is bright or dark or whether sunlight exists and also without being influenced by external disturbance factors.

To attain the objects described above, according to the present invention, there is provided a sugar concentration gauge of a type for measuring the sugar concentration of test liquid applied to a light incidence surface of a prism through detection of a refraction angle, with which a light beam having passed through the test liquid is emitted from the prism which corresponds to the sugar concentration of the test liquid. The sugar concentration gauge comprises a movable plate capable of adjustment with respect to the light incidence surface of the prism, a light incidence plate provided on the movable plate so as to be superposed on the light incidence surface of the prism, and a weight provided on the movable plate to exert a vertical load onto the light incidence surface of the prism, whereby the test liquid can be uniformly spread on the light incidence surface of the prism without being influenced by the kind and amount of the test liquid.

With the weight provided on the movable plate capable of adjustment with respect to the prism surface for providing a vertical load thereto, the test liquid film between the light incidence plate and the prism surface can be given a uniform vertical load and can be made uniformly thin. Thus, the accuracy of measurement can be improved. The test liquid thus can be spread over the entire light incidence surface of the prism, and the measurement of the sugar concentration can be made with a small quantity of test liquid.

According to the present invention, there is provided a sugar concentration gauge which comprises a casing having a light-blocking cover mounted thereon for opening and closing the casing, a prism having a light incidence surface on an open plane of the casing which is closable with the light-blocking cover, a light incidence plate on the light-blocking cover to be superposed on the light incidence surface of the prism, and a light source lamp in the vicinity of the light incidence plate for providing a light beam to test liquid applied to the light incidence surface of the prism, whereby the measurement of the sugar concentration of the test liquid can be made with the light source provided inside the casing closed with the light-blocking cover.

With the construction of the sugar concentration gauge according to the present invention as described above, therefore, it is possible to make measurements of the sugar concentration regardless of whether the ambient condition is bright or dark or whether sunlight exists and without being influenced by external disturbance factors.

The aforementioned objects and other objects, characteristic features and advantages of the present invention will become more apparent to those skilled in the art as the disclosure is made in the following description of a preferred embodiment of the invention, as illustrated in the accompanying drawings.

DETAILED DESCRIPTION OF THE PREFERRED EMBODIMENT

Figure 2:
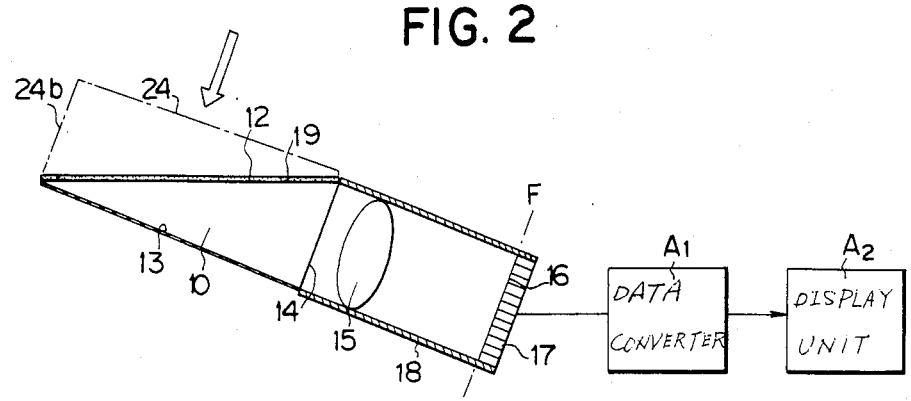
FIG. 2 is a schematic side view illustrating one embodiment of a sugar concentration gauge according to the present invention and the principle mechanism thereof.
Figure 3:
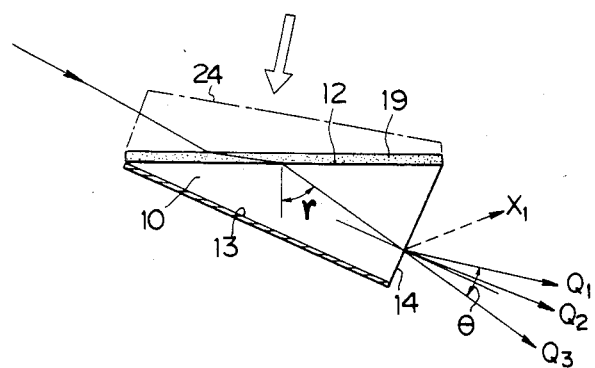
FIG. 3 is an explanatory side view illustrating the state in which a light beam passed through test liquid is transmitted through a prism of the embodiment.
Figure 4:
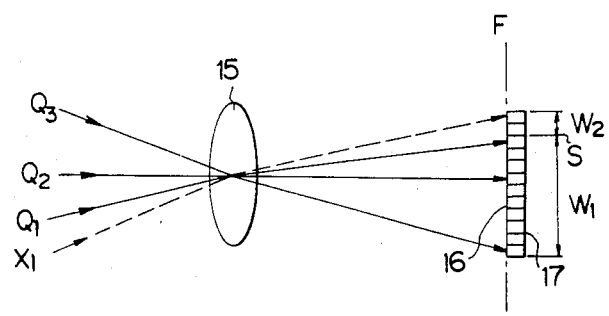
FIG. 4 is an explanatory side view illustrating the state in which the light beam transmitted through the prism is transmitted to a focusing lens and is received by an image sensor of the embodiment.

The present invention will now be described with reference to the illustrated embodiment. FIGS. 2 to 4 illustrate a principle mechanism of a sugar concentration gauge embodying the present invention and a method for measuring the sugar concentration of test liquid.

Figure 1A:
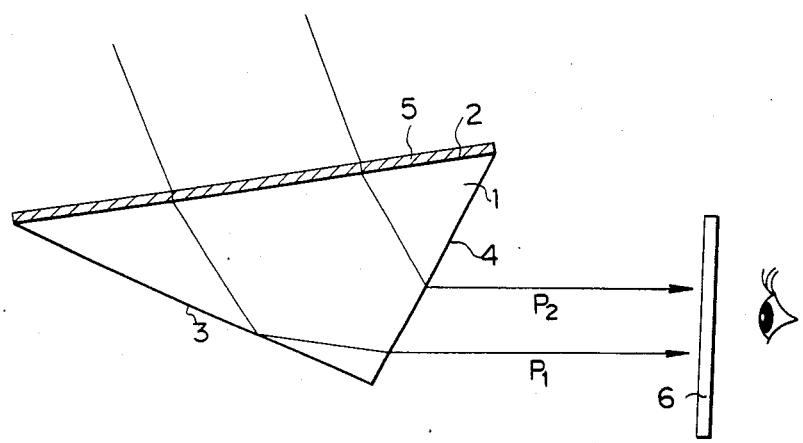
FIG. 1A is a schematic explanatory view illustrating the principle of a prior art sugar concentration gauge utilizing a prism, a gauge plate and light beams transmitted to test liquid.
Figure 1B:
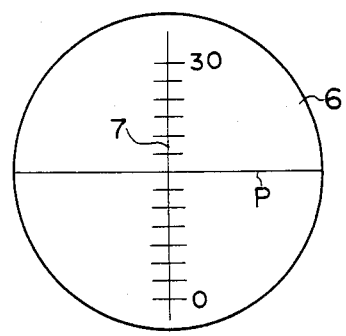
FIG. 1B is a schematic view illustrating the gauge plate of the prior art sugar concentration gauge as seen from a small eyepiece window.

A prism 10 has first second and third surfaces 12, 13 and 14 serving respectively as a light incidence surface, a light absorption surface and a light emission surface. In this embodiment, the second surface 13 is a light absorption surface instead of colored reflecting surface 3 as in the prior art prism 1 shown in FIG. 1A. That is to say, this surface 13 is a black surface to prevent the emission of light reaching this surface, i.e. to prevent light from reflecting from this surface as much as possible to eliminate external disturbance factors. The light which has not reached the light absorption surface 13 but has been passed through test liquid 19 is then emitted as a light beam for sugar concentration measurement from the light emission surface 14. There is provided a focusing lens 15 that faces the light emission surface 14 of the prism 10. An image sensor 16 is disposed at the focal plane F of the focusing lens 15. The light emission surface 14, focusing lens 15 and image sensor 16 are provided in a light-blocking cylinder 18 such that they face one another to eliminate external disturbance factors. The image sensor 16 is a package which includes a plurality of photoelectric conversion elements (semiconductor elements) 17, e.g. photo-transistors, arranged in an array and an IC for converting the outputs of the elements 17 into an electric signal. The surface of the photoelectric conversion element array constitutes a light incidence window. The critical emission angle of the light beam emitted from the prism 10 varies substantially in proportion to the sugar concentration. This phenomenon has been used in the adoption of the image sensor 16.

More specifically, where the light incidence surface 12 of the prism 10 is coated with the test liquid 19 and covered with a light incidence plate 24, as illustrated in FIG. 3, light incident on the light incidence plate 24 is randomly reflected by its glass surface kept in contact with the test liquid into light beams directed in all directions. However, a light beam transmitted through both the test liquid and the light incidence surface 12 of the prism in contact with the test liquid (i.e. the light beam proceeding through the prism) has to only exist within a critical angle $\gamma$ which is determined by the refractive indices of the test liquid 19 and the prism 10. The light beam at the critical angle $\gamma$ is referred to as a critical light beam $Q_1$. The critical light beam $Q_1$ is emitted from the light emission surface 14 of the prism 10 at a refraction angle $\theta$. The light beam emitted from the prism 10, therefore, is within the angle $\theta$. In other words, there exists no emitted light beam at an angle more than the angle $\theta$, such as a light beam $X_1$. The critical light beam $Q_1$, which is emitted with the angle $\theta$ proportional to the sugar content of the test liquid, is passed through the focusing lens 15 to be incident on the image sensor 16 provided at the focal plane F of the lens 15.

Referring to FIG. 4, designated by $Q_1$ a critical light beam is emitted from the prism 10 with an angle $\theta$ of elevation and is incident on the lens 15. The light beam which is passed through the lens 15 and received by the image sensor 16 exists within the emission angle of the critical light beam $Q_1$. Light beams below the position of image produced by the critical light beam $Q_1$, e.g. light beams $Q_2$ and $Q_3$, produce bright images. Hence, the position at which the critical light beam $Q_1$ is received is referred to as a border line S between bright and dark sections. The section below the border line S is referred to as a bright section $W_1$, and the section above the border line as a dark section $W_2$. The border line S between the bright and dark sections $W_1$ and $W_2$ thus is variable vertically in proportion to the sugar concentration of the test liquid, with the photoelectric conversion elements 17 in the bright section $W_1$ being irradiated. In other words, the photoelectric conversion elements 17 that are found in the section corresponding to the sugar concentration of the test liquid are rendered operative to provide an electric signal (i.e. voltage).

This electric signal is transmitted to a data converter $A_1$ for conversion into a digital or analog signal representing the sugar concentration. The converted signal is transmitted to a display unit $A_2$. The sugar concentration of the test liquid 19 thus can be clearly displayed as a digital or analog display on the display unit $A_2$.

Figure 5:
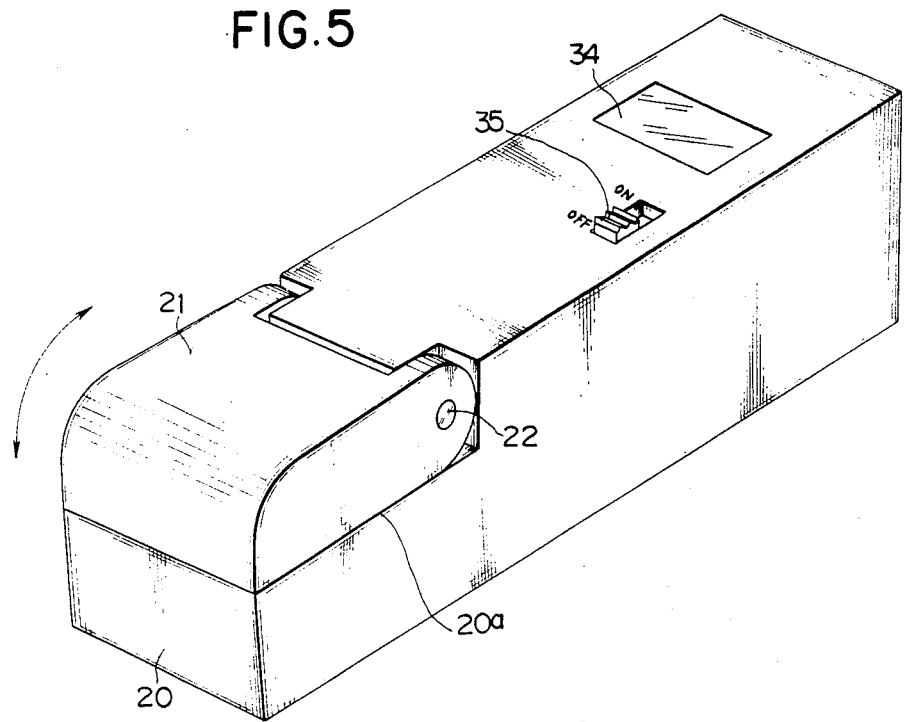
FIG. 5 is a perspective view illustrating the external appearance of the embodiment.

The prism 10, focusing lens 15, image sensor 16, data converter $A_1$ and display unit $A_2$ shown in FIG. 2 are accommodated in a sugar concentration gauge casing 20 as shown in FIG. 5. The prism 10 is secured to the casing 20 such that its light incidence surface 12 is found on an open plane 20a of the casing 20. The open plate 20a is covered with a light-blocking cover 21. The cover 21 is rotated about a hinge 22 at one end thereof to expose and cover the open plane 20a of the casing 20.

Figure 6:
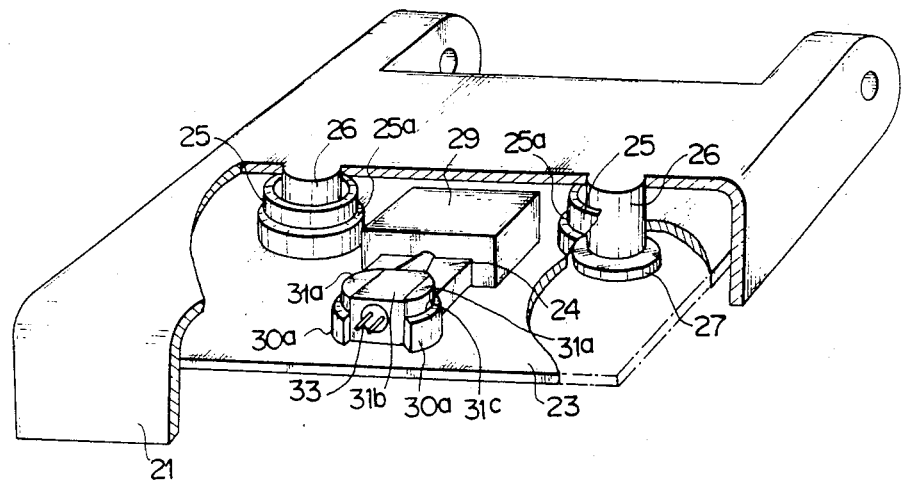
FIG. 6 is a partially cutaway perspective view illustrating an inside construction of light-blocking cover of the embodiment.
Figure 7:
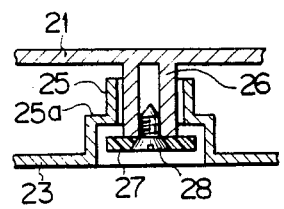
FIG. 7 is a cross section illustrating a movable mechanism for a movable plate and the light-blocking cover of the embodiment.
Figure 8:
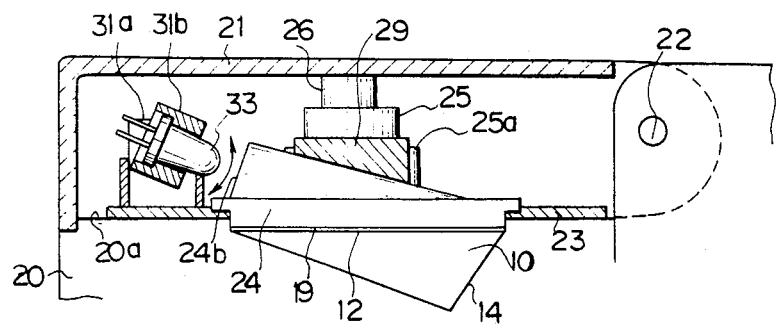
FIG. 8 is a cross section illustrating the internal mechanism of the light-blocking cover of the embodiment.

As illustrated in FIGS. 6 to 8, a movable plate 23 is provided inside the cover 21. The light incidence plate 24 is mounted on the central portion of the movable plate 23. The movable plate 23 is provided on the upper surface thereof and on opposite sides of the light incidence plate 24 having stepped cylindrical projections 25 each with a shoulder 25a provided at an axially intermediate position. Guide posts 26 depending from the inner surface of the cover 21 loosely extend within the cylindrical projections 25. The movable plate 23 is retained by flanges 27 which are secured by screws 28 to the lower ends of the guide posts 26 and can engage the shoulders 25a of the cylindrical projections 25. The movable plate 23 is thus movable in transverse or twisting directions within the range of the gap defined between each guide post 26 and each cylindrical projection 25 loosely surrounding the guide post 26. The movable plate 23 is also movable vertically within a range constituted by the sum of the gap between the lower or inner surface of the cover 21 and the top of each cylindrical projection 25 and the gap between the shoulder 25a of each cylindrical projection 25 and each flange 27. It is understood that the orientation of the movable plate 23 is adjustable with respect to the light incidence surface 12 of the prism 10 within the ranges noted above.

Further, a weight 29 is provided on the top of the movable plate 23 such that it straddles the light incidence plate 24. The light incidence plate 24 is adapted such that its bottom is superposed on the light incidence surface 12 of the prism 10 via the test liquid 19. The capability of orientation adjustment of the movable plate 23 and the provision of the weight 29 on the top of the movable plate 23 cooperatively permit application of uniform vertical load to the test liquid 19. The test liquid 19 thus can be thinly spread uniformly between the prism 10 and the light incidence plate 24 to provide for uniform transmission of light.

Further, in this embodiment, a light source 33 (i.e. a LED) is provided on the top of the movable plate 23 surrounded by the cover 21 so as to face one end of the light incidence plate 24 serving as a light incidence surface 24b. The light source 33 is capable of adjustment so that light can be incident on the light incidence plate 24 at the best angle.

Reference numeral 35 in FIG. 5 designates a power switch for supplying power to the individual parts of the sugar concentration gauge.

Figure 9:
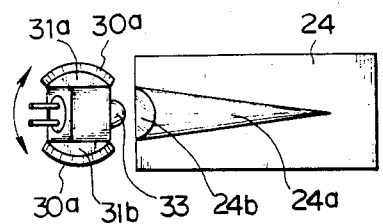
FIG. 9 is a plan view illustrating the arrangement of a light source lamp and a light incidence plate of the embodiment.
Figure 10:
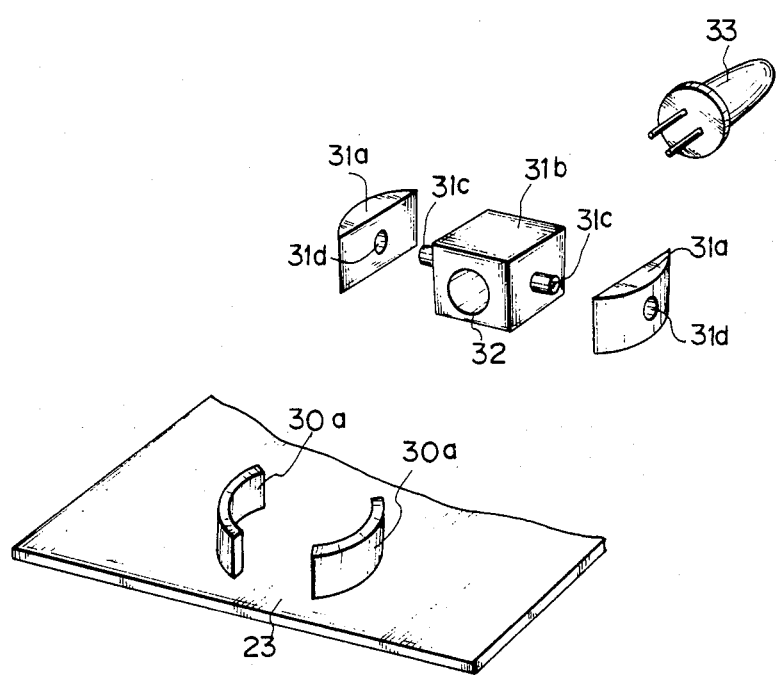
FIG. 10 is an exploded perspective view illustrating a lamp holder of the embodiment.

Referring now to FIGS. 8 to 10, the top of the movable plate 23 is provided with a pair of arcuate guides 30a which form part of a circle and are located ahead of the light incidence surface 24b of the light incidence plate 24. A light source holder is constituted by a pair of rotatable members 31a having arcuate outer sides and a light source support block 31b provided between the rotatable members 31a. The light source support block 31b has a central bore 32, in which the light source 33 is held. The rotatable members 31a are rotatably assembled on the opposite sides of the light source support block 31b by engagement of ears 31c on the block 31b in holes 31d of the members 31a. The light source holder assembled in this way is fitted between the pair of arcuate guides 30a such that the outer arcuate surfaces of the rotatable members 31a can slide along the inner surfaces of the guides 30a. The light source 33 is inserted into the bore 32 of the light source support block 31b. The light source holder is thus rotatable between a pair of arcuate guides 30a via the rotatable members 31a in the directions of arrows in FIG. 9. In addition, the light source support block 31b is rotatable in a vertical plane between the rotatable members 31a in the directions of arrows shown in FIG. 8. When the light source 33 has been set in the best orientation, the component parts of the light source holder are secured together by means of an adhesive, and also the light source holder is secured to guides 30a again by means of an adhesive.

The light incidence plate 24 is provided at the top thereof with a light guide section 24a having a triangular sectional profile. The light source holder is set such that the light source 33 faces the end of the light guide portion 24a. At this time, the light incidence surface 24b of the plate 24 and the light source 33 are inclined relative to the light incidence surface 12 of the prism 10 at a fixed angle.

With the above construction, light from the light source 33 enters the light guide section 24a through the light incidence surface 24b of the light incidence plate 24 to be incident on the test liquid 19 at a certain incidence angle. The light incidence plate 24 may be just a rectangular parallelepiped as well.

As has been described above, the light incidence surface 12 of the prism 10 is covered with the cover 21. The light incidence plate 24 and the light source 33 are accommodated in the cover 21, and the light incidence plate 24 is superposed on the light incidence surface 12 of the prism 10 when the cover 21 is closed.

Measurement of the sugar concentration is thus possible under a condition, under which natural light cannot be secured. In addition, when natural light is utilized, external disturbance factors are removed, and measurement can be carried out stably under fixed conditions.

The result of measurement effected within the sugar concentration gauge casing 20 is displayed on a display window 34 provided on the top of the casing 20 for observation from the outside as shown in FIG. 5.

As has been described in the foregoing, according to the present invention there is provided a sugar concentration gauge of a type for measuring the sugar concentration of test liquid through detection of a refraction angle, with which a light beam having been transmitted through the test liquid is emitted from a prism and which corresponds to the sugar concentration of the test liquid. The sugar concentration gauge, unlike that of the prior art in which the test liquid is applied to the light incidence surface of a prism with or without a frosted glass superposed on it for measurement, comprises a movable plate capable of adjustment with respect to the light incidence surface of the prism, a light incidence plate on the movable plate so as to be superposed on the light incidence surface of the prism, and a weight on the movable plate to exert a vertical load onto the light incidence surface of the prism. Thus, the test liquid can be given a uniform load by the synergistic effect of the movable plate and the weight so that it is spread uniformly into a test liquid film having a uniform thickness. At the same time, the test liquid can be made uniformly thin to a proper extent to permit transmission of light without reducing the quantity of the light transmitted.

It is thus possible to effectively overcome the drawbacks of the prior art of intensity fluctuations of transmitted light or insufficient light transmission due to thickness fluctuations or excessive thickness of the test liquid film even when the test liquid has high viscosity. Stable and highly reliable measurement of the sugar concentration can thus be obtained.

According to the present invention, there is also provided a sugar concentration gauge of a type for measuring the sugar concentration of test liquid through detection of a refraction angle, with which a light beam having been transmitted through a test liquid is emitted from the prism and which corresponds to the sugar concentration of the test liquid. The sugar concentration gauge, unlike that of the prior art in which the measurement is made with natural light introduced into the prism light incidence surface coated with the test liquid and exposed to the outside, comprises a casing having a light-blocking cover mounted thereon for opening and closing the casing, a prism on an open plane of the casing which is closed with the cover, a light incidence plate on the cover to be superposed on the light incidence surface of the prism, and a light source lamp in the vicinity of the light incidence plate for providing a light beam for measurement. Thus, it is possible to make sugar concentration measurement under stable conditions without being influenced by external conditions.

Further, the invention permits measurement even under a condition where natural light cannot be obtained. Further, where natural light is utilized, accurate and highly reliable measurement can be realized by removing external disturbance factors.

Moreover, with the sugar concentration gauge according to the present invention, it is only necessary to open the light-blocking cover, supply drops of test liquid and then close the cover, whereby proper orientations and positions of the light incidence plate and the light source relative to the prism can be obtained to be ready for measurement.

What is claimed is:

1. A sugar concentration gauge for measuring the concentration of sugar in a test liquid by analyzing light passing through the test liquid, said gauge comprising:

a casing having a prism mounted thereto, said prism having a light incidence surface facing and open to the exterior of said casing for receiving the test liquid and through which the light passes after passing through the test liquid;

a cover means pivotably mounted to said casing for pivoting relative to said casing for opening and closing over the exterior of said casing which the light incidence surface of said prism faces and is open to;

a movable plate connected to said cover means so as to be relatively movable thereto, said plate being disposed over the light incidence surface of said prism when said cover means is closed;

a light incidence plate means for allowing light to pass therethrough to the test liquid, said light incidence plate means being fixed in said movable plate so as to pass light through said movable plate and to be movable relative to said cover means with said movable plate and for covering the light incidence surface of said prism and pressing the test liquid on said light incidence surface when said cover means is closed; and means for detecting the light passing through said light incidence plate, the test liquid and said prism so that the light may be analyzed to determine the sugar concentration of the text liquid.

2. A gauge as claimed in claim 1 and further comprising, a weight means fixed to said movable plate so as to be movable relative to said cover means therewith for exerting a load on said movable plate so that said light incidence plate exerts a uniform pressure over the test liquid when the light incidence plate presses the test liquid on said light incidence surface when said cover means is closed.

3. A gauge as claimed in claim 1 wherein, said cover means is a light blocking cover means for blocking out ambient light from the light incidence surface of said prism; and said gauge further comprises a light source means fixed to said movable plate so as to be movable relative to said cover means with said movable plate and for emitting the light that passes through said light incidence plate, the test liquid and said prism when said cover means is closed.

* * * * *